(12) United States Patent
Luo

(10) Patent No.: US 9,280,001 B2
(45) Date of Patent: Mar. 8, 2016

(54) CLEANING ASSEMBLIES FOR EYEGLASSES

(71) Applicant: William Luo, Endeavour Hills (AU)

(72) Inventor: William Luo, Endeavour Hills (AU)

(73) Assignee: William Luo, Endeavour Hills, Victoria (AU)

( * ) Notice: Subject to any disclaimer, the term of this patent is extended or adjusted under 35 U.S.C. 154(b) by 0 days.

(21) Appl. No.: 14/410,931

(22) PCT Filed: Jun. 28, 2013

(86) PCT No.: PCT/AU2013/000700
§ 371 (c)(1),
(2) Date: Dec. 23, 2014

(87) PCT Pub. No.: WO2014/000043
PCT Pub. Date: Jan. 3, 2014

(65) Prior Publication Data
US 2015/0323814 A1    Nov. 12, 2015

(30) Foreign Application Priority Data

Jun. 28, 2012   (AU) ................................. 2012902744
Apr. 11, 2013   (AU) ................................. 2013203729

(51) Int. Cl.
*G02C 1/00*      (2006.01)
*G02C 13/00*     (2006.01)
*G02C 11/08*     (2006.01)

(52) U.S. Cl.
CPC .............. *G02C 13/006* (2013.01); *G02C 11/08* (2013.01)

(58) Field of Classification Search
CPC ........................................................ G02C 11/08
USPC ................... 351/158, 41; D16/330, 309, 312; 15/250.3, 250.27
See application file for complete search history.

(56) References Cited

U.S. PATENT DOCUMENTS

| | | | | |
|---|---|---|---|---|
| 2,888,703 A | * | 6/1959 | Karwowska | G02C 11/08 15/250.27 |
| 4,789,233 A | * | 12/1988 | Arsenault | G02C 13/006 15/250.04 |
| 6,640,379 B1 | * | 11/2003 | Scribner | G02C 11/08 15/250.27 |
| 6,722,766 B1 | | 4/2004 | Myette | |
| D676,078 S | * | 2/2013 | Lynch | D16/309 |

FOREIGN PATENT DOCUMENTS

| | | |
|---|---|---|
| CN | 201540415 U | 8/2010 |
| CN | 201698113 U | 1/2011 |

OTHER PUBLICATIONS

International Search Report for PCT/AU2013/000700, ISA/AU, Woden ACT, mailed Aug. 21, 2013.

* cited by examiner

*Primary Examiner* — Hung Dang
(74) *Attorney, Agent, or Firm* — Harness, Dickey & Pierce, P.L.C

(57) ABSTRACT

A cleaning assembly for eyeglasses having at least one lens supported by a frame including at least one aperture substantially the size of a cross section of the at least one lens, wherein the aperture can fit at least one cleaning element and adapted to move relative to the at least one lens to clean the exposed surface of the lens.

12 Claims, 3 Drawing Sheets

CLEANING ASSEMBLIES FOR EYEGLASSES

FIELD OF THE INVENTION

The present invention relates to cleaning assemblies for eyeglasses and their methods of manufacture.

BACKGROUND TO THE INVENTION

Eyeglasses, also known as glasses, spectacles or even specs are conventionally known as frames holding one or more lenses in front of the eyes. Eyeglasses can include goggles or masks with lenses. Eyeglasses serve a variety of purposes including: correction of deficient vision, protection sunlight or other hazards, for viewing or decoding visual information such as three-dimensional movies or for aesthetic or fashion purposes.

A disadvantage to using eyeglasses is their inconvenience from reduced visibility if the surfaces of the lenses become covered with materials such as water condensation, dust or other opaque materials. Conventional methods of cleaning eyeglasses include using cloths or other sheets with or without cleaning fluids. However, this is inconvenient as the eyeglasses must be removed from the wearer. This then results in a temporary loss of vision or protection which can also increase the danger to the wearer, if they are doing high-risk activities or are protecting from radiation. It can also interrupt playing sport activities and further it is inconvenient for the wearer to carry the sheets or tissues and cleanings fluids on their person.

In view of the above, it is desirable to produce safer and more effective ways to clean eyeglasses. However, equipping separate wiper components on frames can be complex to manufacture given the thinly shaped frame of conventional eyeglasses. In terms of aesthetical appearance, it is acceptable to wear eyeglasses with only frame and fitted lenses. But unlike wipers for cars, it is not aesthetical to wear eyeglasses that have separate wiper components Therefore, an advanced cleaning assembly for eyeglasses is preferable to resolve the mentioned manufacturing and aesthetical problems.

SUMMARY OF THE INVENTION

An eyeglass including;
a frame;
at least one lens supported by the frame; and
the frame including at least one wiper element;
wherein the at least one wiper element and the at least one lens is adapted to move relative to each other to clean an exposed surface of the lens; and
wherein the frame includes at least one aperture substantially the size of a cross section of the at least one lens such that the lens is movable within the frame with respect to the frame.

The at least one aperture can include at least one wiper element. Preferably, at least one lens can be movable with respect to the at least one wiper element to clean an exposed surface of the lens. Thus, the cleaning assembly may include at least one wiper element within the frame of the eyeglasses to provide an efficient way of cleaning the eyeglasses where the wiper element is integral to the eyeglasses.

The at least one wiper element can clean both surfaces of the lens. Preferably, the at least one wiper element cleans both surfaces of the at least one lens simultaneously. This provides the advantage of cleaning the eyeglasses quickly and efficiently, and allows the inner surface of the lens to be cleaned without removal of the eyeglasses.

In another embodiment, the assembly can include at least one reservoir. Preferably, the at least one reservoir is refillable and can include at least one dispenser for dispensing fluid to the at least one wiper element. Preferably, the at least one reservoir includes fluid for cleaning the at least one lens.

These features provide the user with convenient access to cleaning materials so that these are not required to be carried separately. Preferably, at least one component of the assembly is releasably attachable such that the at least one wiper element or any other cleaning assembly component can be exposed or removed or replaced. Thus the at least one wiper element can be exposed for cleaning, removed for replacement purposes, replaced or any other similar reason.

BRIEF DESCRIPTION OF THE DRAWINGS

In order that the present invention can be more readily understood, preferred embodiments thereof will now be described, by way of example only, with reference to the accompanying drawings, in which:

FIGS. 1a and 1b show perspective views of embodiment of the present invention of eyeglasses where the lens is movable through an aperture in the frame, while

DESCRIPTION OF PREFERRED EMBODIMENT

Figure 1A:
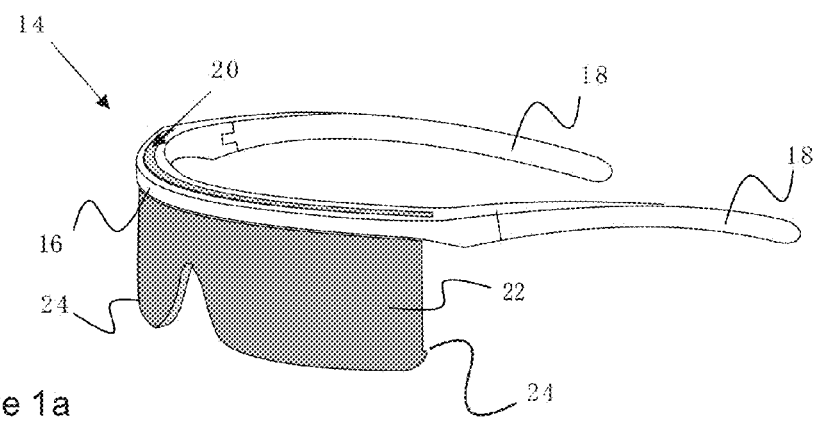
Figure 1B:
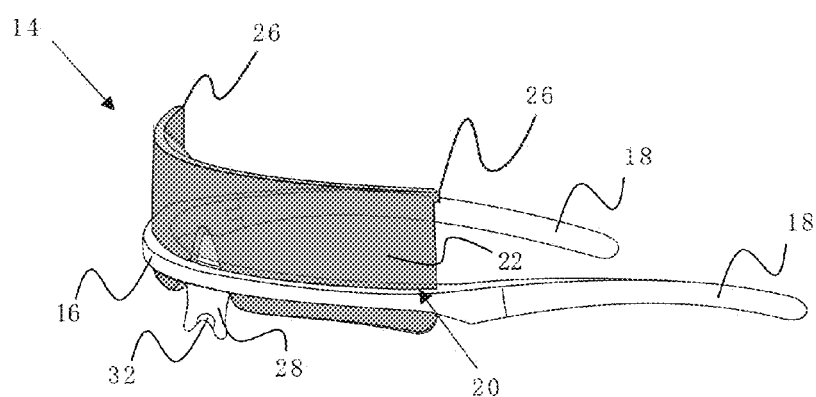
Figure 1C:
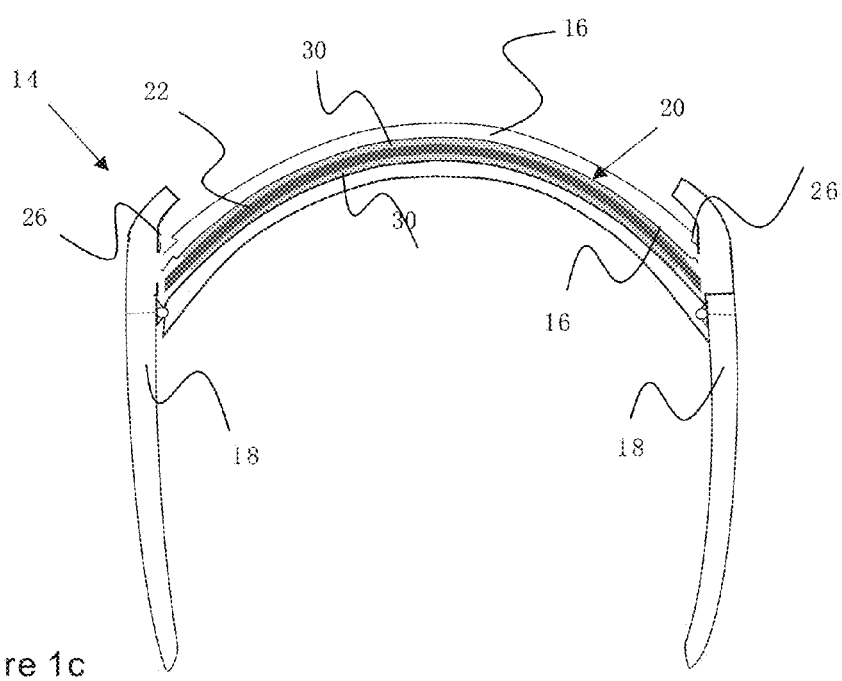
FIG. 1c shows a cross sectional view of the eyeglasses of FIGS. 1a and 1b.

FIGS. 1a to 1c show cleaning assembly 14 which include the frame 16 that does not form a rim around the edges of the lens 22, but where the frame 16 includes an aperture 20 that is substantially the size of a cross-section of the lens 22. The frame 16 may also include arms 18. The lens 22 is therefore able to pass substantially through the aperture 20. Aperture 20 is fitted with two cleaning elements 30, one on each side of the inner surface of the aperture 20, as exemplified in FIG. 1c which shows a cross sectional view of FIG. 1a. When the lens 22 passes through the aperture 20, the cleaning elements 30 remove any unwanted particulates or fluids from the lens 22. FIG. 1a shows the cleaning assembly 14 where the lens 22 is in a position for use for viewing or for protection. When the lens 22 is dirty, the lens 22 can be manually manipulated through the aperture 20 by the user, as shown in FIG. 1b. Protrusions 24, 26 at the corners of the lens 22 prevent the lens 22 from disengaging from the frame 16. The support element 28 may also be utilised to prevent unwanted movement of the lens 22 by additional protrusions 32. Cleaning assembly 14 provides the advantages for cleaning both the interior and exterior surfaces of the lens 22 without removing the cleaning assembly 14 from the user, particular for users who have fogged up the interior surface of their lens 22. Another advantage is that the frame 16 includes the wiper element such that the wiper element is not a separate component. This simplifies manufacturing processes for the cleaning assembly 14 and is more aesthetically acceptable for users to wear.

The at least one wiper element 16 of FIG. 1b can includes a support element 28 which is shaped to fit on a user's nose in the middle of the at least one wiper element 16. When the eyeglasses are positioned on a person's face for viewing or protection, the support element 28 supports the wiper element 16 such that the wiper element 16 is kept at the top of the lens 22. This helps to keep the at least one wiper element 16 out of the user's field of vision until the wiper element 16 is required for cleaning.

Figure 2A:
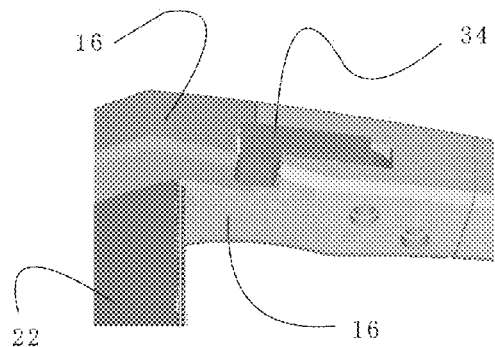
FIGS. 2a to 2c show exploded views of the eyeglasses of FIGS. 1a to 1c where the cleaning elements are detachable from the frame.
Figure 2B:
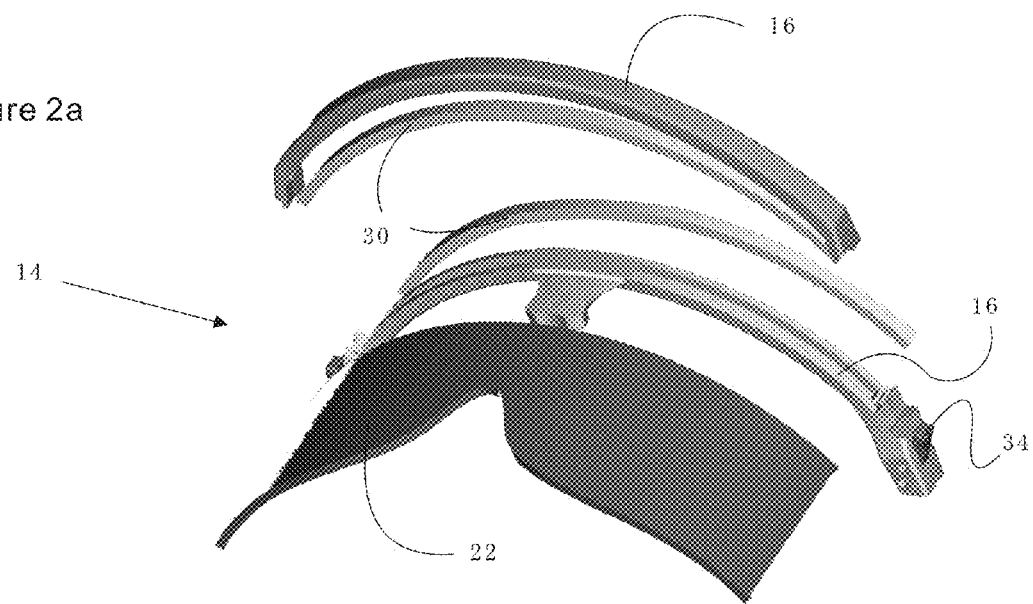
Figure 2C:
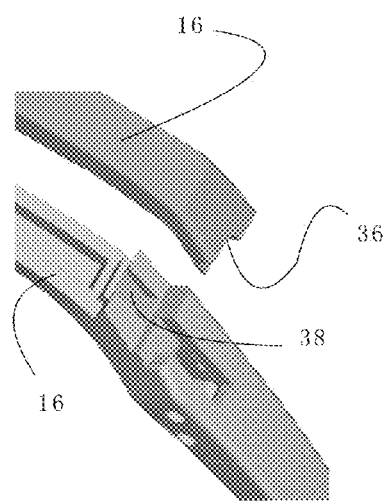

The cleaning assembly 14 can have one or more parts that are removably detachable and which are secured by one or more fasteners 34, as shown in FIGS. 2a to 2c. In particular, the exploded view of the cleaning assembly 14 of FIG. 2b shows that the internal structure of the frame 16, lens 22 and/or any part or whole of the wiper elements, cleaning elements 30 can be exposed or removed for replacement, repair, cleaning or any other purpose. A fastener 34 such as a clip, screw or pivoting catch can be used to secure all the components of the cleaning assembly 14, as shown in close up view of the corner of the frame 16 in FIG. 2a. Once the fastener 34 is undone, as illustrated in FIG. 2c, the frame 16 can be pulled apart in two or more pieces to reveal individual cleaning elements 30. Even lens 22 can be replaced for one of a differing magnification or colour. A series of flanges and recesses, 36, 38 allow the frame 16 to interlock.

Figure 3A:
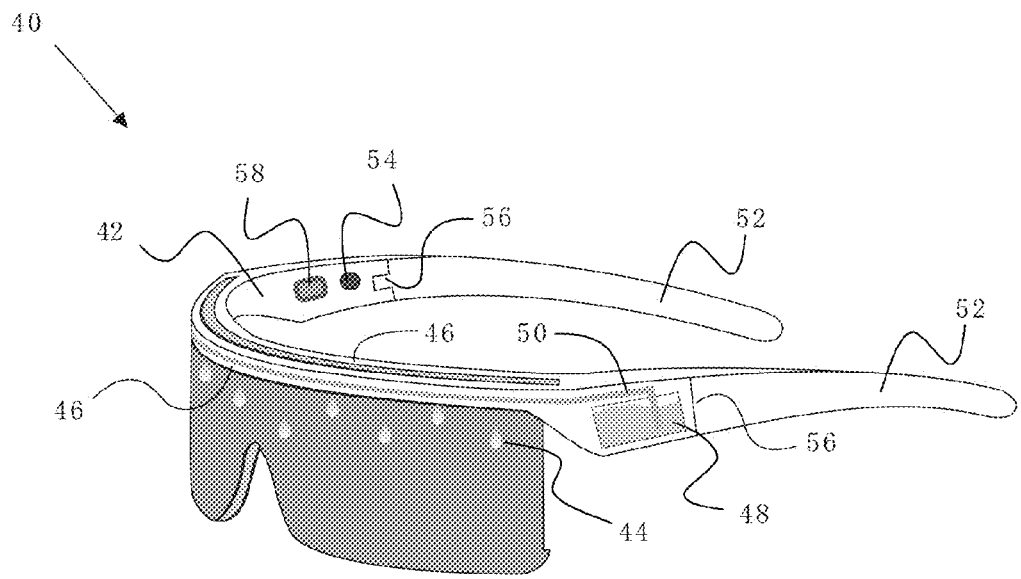
FIGS. 3a and 3b show perspective views of yet another embodiment of the invention including a reservoir for cleaning fluid.
Figure 3B:
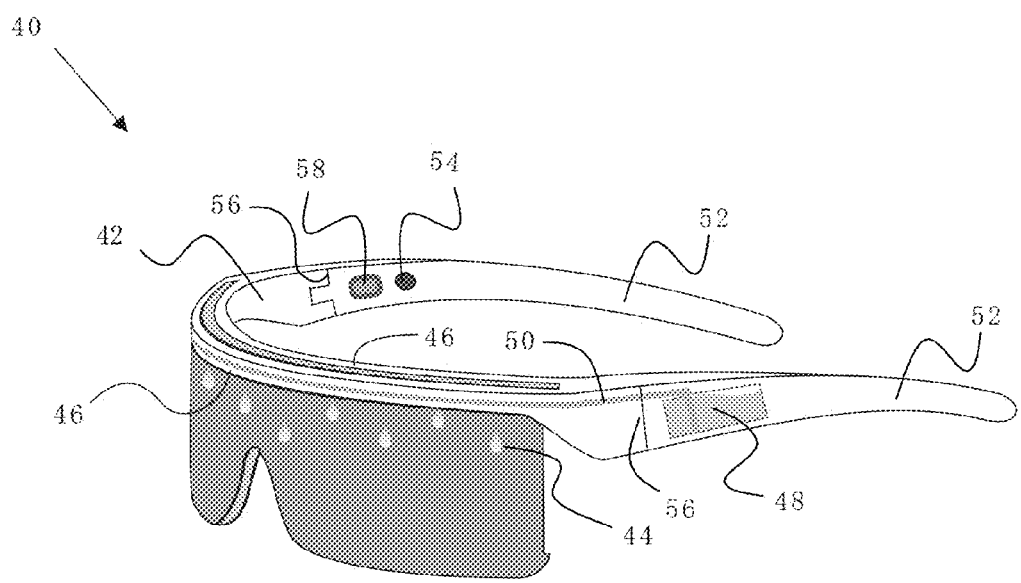

The cleaning assembly described above can also include at least one reservoir 48 for containing cleaning fluids or other liquids 44. As described in FIGS. 3a and 3b. In FIG. 3a, the at least one reservoir 48 is located in the cleaning assembly 40 within the frame 42. The frame 42 can also includes the arms 52 which can be connected via a hinge 56. In FIG. 3b, the at least one reservoir 48 is located in the cleaning assembly 60 specifically within the arm 52 of the frame 42. The cleaning fluid 44 can be dispensed onto the cleaning element of the wiper element 46 on either side of the cleaning assembly 40 and 60 via passageway 50. The reservoir 48 can also be refilled via an aperture 54 and cleaning fluid 44 released by pressing button 58.

Further modifications and improvements can be made without departing from the scope of the present invention. For example, the cleaning elements can be made of any suitable material for cleaning glass or plastic lens, including microfiber materials, cotton or synthetic cloths.

The invention claimed is:

1. An eyeglass including:
    a frame;
    at least one lens supported by the frame; and
    the frame including at least one wiper element;
    wherein the at least one wiper element and the at least one lens is adapted to move relative to each other to clean an exposed surface of the lens; and wherein the frame includes at least one aperture substantially the size of a cross section of the at least one lens such that the least one lens is movable within the frame with respect to the frame.

2. The eyeglass according to claim 1, wherein the at least one aperture includes at least one wiper element.

3. The eyeglass according to claim 1, wherein the at least one wiper element cleans both surfaces of the at least one lens.

4. The eyeglass according to claim 1, wherein the at least one wiper element cleans both surfaces of the at least one lens simultaneously.

5. The eyeglass according to claim 1, wherein the at least one wiper element includes at least one cleaning element.

6. The eyeglass according to claim 1, wherein the at least one wiper element includes two cleaning elements.

7. The eyeglass according to claim 1, including at least one reservoir.

8. The eyeglass according to claim 7, including at least one reservoir that is re-fillable and/or includes at least one dispenser for dispensing fluid to the at least one wiper element.

9. The eyeglass according to claim 8, wherein the at least one reservoir includes fluid for cleaning the at least one lens.

10. The eyeglass according to claim 7, wherein the at least one reservoir includes fluid for cleaning the at least one lens.

11. The eyeglass according to claim 1, wherein at least one component of the assembly is releasably attachable such that the at least one wiper element can be exposed or removed or replaced.

12. The eyeglass according to claim 1, wherein the frame includes a support element such that the support element is adapted to support the frame on a user's nose.

* * * * *